United States Patent [19]

Neumann et al.

[11] 4,430,181
[45] Feb. 7, 1984

[54] PROCESS FOR THE PREPARATION OF BENZOYL CHLORIDE

[75] Inventors: Rainer Neumann; Karl Morgenstern; Karl-August Lipper; Friedrich Brühne; Walter Böckmann; Clemens Casper; Siegfried Zingel, all of Krefeld, Fed. Rep. of Germany

[73] Assignee: Bayer Aktiengesellschaft, Leverkusen, Fed. Rep. of Germany

[21] Appl. No.: 436,108

[22] Filed: Oct. 22, 1982

[30] Foreign Application Priority Data

Nov. 7, 1981 [DE] Fed. Rep. of Germany ....... 3144316

[51] Int. Cl.³ .................. B01J 19/12; C07C 63/10
[52] U.S. Cl. .................. 204/158 HA; 260/544 D
[58] Field of Search ............ 204/158 HA; 260/544 D

[56] References Cited

U.S. PATENT DOCUMENTS 2,865,959  12/1958  Toland .................. 204/158 HA 3,899,532  8/1975  Lanet .................. 260/544 D

OTHER PUBLICATIONS

DE-A-1 070 616 (Chem. Werke Witten), Anspruch; Spalte 1, Beispiel 1.
DE-A-1 909 523 (Farbenfabriken Bayer) Anspruch; Seite 1, Absatz 4–Seite 2, Zeile 9.
EP-A-0 019 341 (Stamicarbon), Anspruch 1; Seite 1, Zeilen 16-24.

*Primary Examiner*—Howard S. Williams
*Attorney, Agent, or Firm*—Sprung, Horn, Kramer & Woods

[57] ABSTRACT

Benzoyl chloride is prepared by a process in which the high-boiling residue obtained in the catalytic oxidation of toluene with oxygen or oxygen-containing gases in the liquid phase is largely freed of heavy metal salts which are present, and is then chlorinated at elevated temperatures, optionally under the action of light, and the benzoyl chloride is then separated off.

19 Claims, No Drawings

PROCESS FOR THE PREPARATION OF BENZOYL CHLORIDE

The invention relates to a process for the preparation of benzoyl chloride.

In the preparation of benzoic acid by catalytic oxidation of toluene with oxygen or oxygen-containing gases in the liquid phase (described, for example, in Ullmanns Enzyklopädie der technischen Chemie (Ullmann's Encyclopedia of Industrial Chemistry), 4th edition, volume 8, pages 367–369), a high-boiling tar-like residue which is difficult to put to further use is obtained when the oxidation product is worked up. This residue which is obtained in the working-up, that is to say, as a rule, in the purification of the benzoic acid-containing reaction product by distillation, essentially consists of residual benzoic acid, benzyl benzoate, various isomeric phenylbenzoic acids, diphenyl and various heavy metal salts, such as cobalt salts and manganese salts. Since this residue is produced in an amount of up to 10%, relative to the pure benzoic acid obtained, which is equivalent to a few thousand tons per year in the industrially customary processes, it is worthwhile for economic reasons to work up this residue to obtain products which can be utilized.

A process for the preparation of benzoyl chloride has now been found, which is characterized in that the high-boiling residue obtained in the catalytic oxidation of toluene with oxygen or oxygen-containing gases in the liquid phase is largely freed of heavy metal salts which are present, and is then chlorinated at elevated temperatures, optionally under the action of light, and the benzoyl chloride is then separated off.

Preferably the heavy metal salt content is reduced to no more than 20 ppm, especially no more than 10 ppm, by weight.

In the process according to the invention, the high-boiling, tar-like residue which is obtained in the customary manner, such as, for example by distillation of the oxidation mixture, in the catalytic oxidation of toluene with oxygen or oxygen-containing gases, and which mainly comprises benzyl benzoate (approx. 70 to 75%) and benzoic acid (approx. 10 to 15%), in addition to phenylbenzoic acids, diphenyl and various heavy metal salts, such as cobalt salts and manganese salts (see Ullmanns Enzyklopädie der technischen Chemie, 4. Auflage 8, 367 to 368), which are added in this form to the oxidation as catalysts, is largely freed of the heavy metal salts, which means that the heavy metal salt content is reduced to no more than 20 ppm, especially no more than 10 ppm, by weight.

For example, the heavy metal salts can be separated from the residue by distillation under normal pressure, reduced pressure or elevated pressure. In general, the distillation is carried out at temperatures of about 120° to 330° C., preferably at 180° to 250° C., and under pressures of about 1 to 1,050 mbar, preferably at 20 to 350 mbar. According to this method, a distillate (approx. 70 to 90% of the residue employed) is obtained, which approximately corresponds in its composition to the residue employed, but is largely freed of the heavy metal salts (content of heavy metal salts in the distillate, for example, about 5 ppm).

Furthermore, it is also possible, for example, to separate the heavy metal salts from the residue by extraction with an aqueous carboxylic acid (see Ullmanns Enzyklopädie der technischen Chemie (Ullmann's Encyclopedia of Industrial Chemistry), 4th edition, volume 8, pages 367–369).

The distillate obtained from the benzoic acid residue and largely freed of the heavy metal salts is then, without further processing, completely chlorinated under the conditions customary for side-chain chlorination (see, for example, Ullmanns Enzyklopädie der technischen Chemie (Ullmann's Encyclopedia of Industrial Chemistry), 4th edition, volume 9, page 528), at temperatures of about 80° to 220° C., preferably at 130° to 190° C. The chlorination is customarily carried out in the presence of light (UV irradiation). However, it is also possible to carry out the chlorination in the dark.

In general, the chlorination is carried out using about 2 to 3.5 mols of chlorine, preferably 2.01 to 2.5 mols of chlorine, per mol of benzyl benzoate present. However, provided that lower yields are accepted, it is also possible to carry out the chlorination using less than 2 mols of chlorine per mol of benzyl benzoate.

From the product mixture obtained in the chlorination, pure benzoyl chloride can then be obtained, for example by distillation under normal, reduced or elevated pressure. In general, distillation is carried out at temperatures from about 30° to 200° C., preferably from 80° to 130° C., and under pressures from about 1 to 1,050 mbar, preferably from 20 to 150 mbar. By this method, benzoyl chloride is obtained in a yield of approx. 93%, relative to the benzyl benzoate present in the distillate.

In this manner, benzoyl chloride can be obtained in high yields from the benzyl benzoate constituent of the distillate, and it is surprising that the chlorination is affected neither by residual heavy metal salts nor by other impurities present in the distillate.

To increase the yield of benzoyl chloride, the residue which remains in the distillation of the chlorination mixture and which still contains approx. 5% of benzoyl chloride in addition, inter alia, to benzoic acid and benzoic acid anhydride, can be reacted with benzotrichloride (about 1 to 2 mols, preferably 1 to 1.5 mols, relative to 1 mol in each case of phenylbenzoic acid and benzoic acid still present in the residue and benzoic acid anhydride formed) at temperatures from about 100° to 220° C., preferably 130° to 180° C., in the presence of about $10^{-5}$ to $10^{-1}$ mol, preferably $10^{-4}$ to $10^{-2}$ mol, of Friedel-Crafts catalysts, such as iron(III) chloride, iron(II) chloride and zinc(II) chloride, and/or acids, such as sulphuric acid and/or phosphoric acid, and after the evolution of HCl gas has ceased the mixture can again be fractionally distilled to isolate benzoyl chloride. In this manner, a yield of approx. 92%, relative to benzoic acid present in the distillate, benzyl benzoate which is present, phenylbenzoic acid which is present, and benzotrichloride added, can be obtained.

In this embodiment, it is particularly surprising that both the benzoic acid present and the benzoic acid anhydride, formed in the chlorination product by the reaction of benzoic acid with benzoyl chloride which has already formed, likewise are not chlorinated in the nucleus in spite of the presence of traces of heavy metal salts, and thus can be reacted in the residue with benzotrichloride to give benzoyl chloride, thereby considerably increasing the yield of benzoyl chloride, relative to the total distillate.

In a preferred embodiment of the process according to the invention, the product mixture obtained in the chlorination is reacted further, without being worked up beforehand to give benzoyl chloride, directly with benzotrichloride in the presence of the Friedel-Crafts catalysts mentioned, at temperatures from about 100° to 220° C., preferably 130° to 180° C. In this process, about 1 to 2 mols, preferably 1.01 to 1.5 mols, of benzotrichloride, relative to 1 mol in each case of phenylbenzoic acid and benzoic acid still present in this product mixture and benzoic acid anhydride formed, are employed.

The amount of Friedel-Crafts catalysts is in general about $10^{-5}$ to $10^{-1}$ mol, preferably $10^{-4}$ to $10^{-2}$ mol, per mol of benzoyl chloride formed.

After the end of the reaction, which becomes evident from the fact that the evolution of HCl gas subsides, the reaction mixture is worked up by fractional distillation to obtain benzoyl chloride, as described above. In this process, pure benzoyl chloride is obtained in a yield of approx. 92%, relative to benzoic acid, phenylbenzoic acid, benzyl benzoate and benzotrichloride added.

Using the process according to the invention, benzoyl chloride can be prepared in a simple, economical manner, in good yields, from the tar-like residue as obtained in the preparation of benzoic acid.

Benzoyl chloride is used in large amounts to produce benzophenone, benzamide and benzoic acid anhydride, and serves, in addition, as an intermediate product for dyestuffs and medicaments (see Ullmanns Enzyklopädie der technischen Chemie (Ullmann's Encyclopedia of Industrial Chemistry), 4th edition, volume 8, page 373).

The examples which follow are intended to illustrate the process according to the invention.

EXAMPLE

Benzoic acid residues obtained in the preparation of benzoic acid were evaporated down in a multiphase helical tube evaporator, at temperatures between 200° and 250° C. and under pressures of 30 to 70 mbar. The amount of distillate was between 70 and 90%, relative to the residue employed. The content of cobalt and manganese in the distillate was below 5 ppm. Average composition of the benzoic acid distillate:

| | |
|---|---|
| Benzoic acid | 10 to 15% by weight |
| Benzyl benzoate | 70 to 75% by weight |
| Diphenyl | 0.1 to 0.5% by weight |
| o-, m- and p-phenylbenzoic acid | 8 to 10% by weight |
| Unknown components | 2 to 3% by weight |
| $CO^{2+}$ | 0.3 to 4 ppm by weight |
| $Mn^{2+}$ | 0.05 to 1 ppm by weight |

(a) 1,500 g of a distillate prepared as described above (72.2% of benzyl benzoate, 11.6% of benzoic acid and 10.0% of phenylbenzoic acids) are chlorinated at 170° C. in the dark. After 3.5 hours, the mixture has increased in weight by approx. 380 g by absorption of chlorine.

In a fractional vacuum distillation, 1,336 g of pure benzoyl chloride are obtained (yield 93%, relative to benzyl benzoate employed). 536 g remain as the residue. This contains 5% of benzoyl chloride. 450 g of benzotrichloride are added to this residue at 150° C. in the presence of 0.1% of FeCl₃ (in this step, benzoyl chloride is obtained from benzoic acid and benzoic acid anhydride) in order to convert the benzoic acid constituents into benzoyl chloride.

After the evolution of hydrogen chloride has ended, the mixture is again fractionally distilled in vacuo. 449 g of pure benzoyl chloride are obtained. This corresponds to a yield of 92% (relative to benzoic acid, benzyl benzoate, phenylbenzoic acid and benzotrichloride employed). The residue is 450 g.

(b) 1,000 g of a distillate prepared as described above (74.2% of benzyl benzoate, 13.4% of benzoic acid and 10.0% of phenylbenzoic acid) are chlorinated at 160° C. under irradiation with UV light (mercury vapour lamp). After 5 hours, the mixture has increased in weight by approx. 260 g by absorption of chlorine. 330 g of benzotrichloride and 1,1 g of FeCl₃ are added dropwise to the mixture at 150° C. to convert benzoic acid which is still present and benzoic acid anhydride which has been formed into benzoyl chloride. After the evolution of hydrogen chloride has ended, the mixture is fractionally distilled in vacuo. 1,265 g of pure benzoyl chloride (yield greater than 92%, relative to benzoic acid, benzyl benzoate, phenylbenzoic acid and benzotrichloride added) are obtained in this distillation. 250 g remain in the distillation residue.

(c) 6.2 tons of a distillate obtained from the residue of a benzoic acid production (71.9% of benzyl benzoate, 13.0% of benzoic acid, 9% of phenylbenzoic acid and 6.1% of other compounds) and prepared as described above are chlorinated in an enamel vessel at 160° to 170° C., in the dark. After 37 hours the chlorination is complete.

1. 2,000 g of the chlorination mixture was reacted with benzotrichloride (520 g) and FeCl₃ (1.9 g) at 150° C. to convert benzoic acid into benzoyl chloride. After the evolution of HCl gas has ended, the mixture is fractionally distilled in vacuo. 1,890 g of pure benzoyl chloride are obtained in this procedure (approx. 90% yield).

2. Benzotrichloride (2.0 tons) and FeCl₃ (7.1 kg) are slowly, at 150° to 160° C., to the mixture obtained by chlorination of 6.2 tons of distilled residue to convert the benzoic acid and any benzoic acid anhydride present into benzoyl chloride. After the evolution of HCl gas has ended, a vacuum distillation is carried out. Pure benzoyl chloride is obtained in this distillation (7.3 tons). The yield is about 89%.

What is claimed is:

1. A process for the preparation of benzoyl chloride, whch comprises treating the high-boiling residue obtained in the catalytic oxidation of toluene with oxygen or an oxygen-containing gas in the liquid phase to largely free the same of heavy metal salts and thereafter chlorinating the resultant material, largely freed of heavy metal salts, at an elevated temperature and thereafter separating off benzoyl chloride.

2. A process according to claim 1, wherein the heavy metal salt content is reduced to no more than 20 ppm, by weight.

3. A process according to claim 1, wherein the chlorination is effected under the action of light.

4. A process according to claim 3, wherein the chlorination is effected under the action of ultraviolet irradiation.

5. A process according to claim 1, wherein the chlorination is effected in the dark.

6. A process according to claim 1, wherein the chlorination product, without being worked up beforehand to give benzoyl chloride, is reacted with benzotrichloride in the presence of a Friedel-Crafts catalyst and thereafter benzoyl chloride is separated from the resultant reaction mixture.

7. A process according to claim 6, wherein the reaction of the chlorination product with benzotrichloride is effected at a temperature of 100° to 220° C.

8. A process according to claim 7, wherein between about 1 and 2 mols of benzotrichloride are employed per mol of phenylbenzoic acid and benzoic acid still present in the chlorination reaction product.

9. A process according to claim 7, wherein the Friedel-Crafts catalyst is employed in an amount of $10^{-5}$ to $10^{-1}$ mol per mol of benzoyl chloride to be formed.

10. A process according to claim 1, wherein the chlorination is effected at a temperature of 30° to 220° C. at a pressure from about 1 to 1,050 mbar.

11. A process according to claim 10, wherein the chlorination is effected at a temperature of 80° to 130° C. at a pressure from 20 to 150 mbar.

12. A process according to claim 1, wherein the heavy metal salts are largely separated from the high-boiling residue obtained in the catalytic oxidation of toluene with oxygen or oxygen-containing gas by distillation.

13. A process according to claim 12, wherein the distillation is carried out at a temperature from 120° to 330° C. at a pressure from 1 to 1,050 mbar.

14. A process according to claim 13, wherein the distillation is carried out at a temperature of 180° to 250° C. at a pressure from 20 to 350 mbar.

15. A process according to claim 1, wherein the chlorination is carried out at a temperature of 80° to 220° C.

16. A process according to claim 1, wherein the chlorination is carried out at a temperature of 130° to 190° C.

17. A process according to claim 1, wherein the chlorination is carried out using 2 to 3.5 mols of chlorine per mol of benzyl benzoate present.

18. A process according to claim 1, wherein the chlorination is carried out using 2.01 to 2.5 mols of chlorine per mol of benzyl benzoate present.

19. A process according to claim 1, wherein the benzoyl chloride formed is separated off by distillation.

* * * * *